United States Patent
Gruning et al.

(10) Patent No.: US 6,268,521 B1
(45) Date of Patent: Jul. 31, 2001

(54) PROCESS FOR PREPARING ACRYLIC ESTERS AND/OR METHACRYLIC ESTERS OF POLYOXYALKYLENES AND THE USE THEREOF

(75) Inventors: Burghard Gruning; Geoffrey Hills, both of Essen; Wolfgang Josten, Konigswinter; Dietmar Schaefer, Hattingen; Stefan Silber, Krefeld; Christian Weitemeyer, Essen, all of (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 09/431,448

(22) Filed: Nov. 1, 1999

(30) Foreign Application Priority Data

Nov. 3, 1998 (DE) ................................................ 198 50 541

(51) Int. Cl.[7] ............................ C08F 69/54; C08F 20/26; C08F 120/26
(52) U.S. Cl. ........................ 560/209; 560/205; 560/217; 522/181; 528/271; 526/320; 526/328
(58) Field of Search ..................... 522/181; 526/329.6, 526/328, 320; 528/271; 560/209, 205, 217

(56) References Cited

U.S. PATENT DOCUMENTS 4,528,334    7/1985   Knopf et al. .

FOREIGN PATENT DOCUMENTS

| 195 35 936 A1 | 4/1997 | (DE) . |
|---|---|---|
| 196 54 752 A1 | 7/1997 | (DE) . |
| 0 803 556 A1 | 10/1997 | (EP) . |
| 9-267034 | 10/1997 | (JP) . |

OTHER PUBLICATIONS

K. Ito, "Reactivity of Poly(ethylene oxide) Macromonomers in Radical Copolymerization," Polymer Journal, vol. 17, No. 7, pp. 827–839 (1985).

K. Ito, "Poly(Ethylene Oxide) Macromonomers 3. *Solvent Effects on the Macromonomer's Reactivity in Radical Copolymerization," Polymer Bulletin, vol. 15, pp. 425–430 (1986).

R. Tor, "Enzymatically Catalysed Transesterificationsof Acryl and Methacryl Monomeric Esters," Enzyme Microb. Technol., vol. 12, pp. 299–304 (Apr. 1990).

H. Furuhashi, et al., "Synthesis, Polymerization, and Dispersion Copolymerization of Poly(Ethylene Oxide) Macromonomers Carrying Methacryloylalkyl End Groups," Colloid Polym Sci, vol. 275, pp. 227–233 (1997).

Y. Nagasaki, et al., Synthesis of Heterotelechelic Poly(ethylene glycol) Macromonomers. Preparation of Poly(ethylene glycol) Possessing a Methacryloyl Group at One End and a Formyl Group at the Other End Macromolecules, vol. 30, pp. 6489–6493 (1997).

*Primary Examiner*—Susan W. Berman
(74) *Attorney, Agent, or Firm*—Scully, Scott, Murphy & Presser

(57) ABSTRACT

The present invention provides a process for enzymatic preparation of acrylic esters and/or methacrylic esters of polyoxyalkylenes, and to the use thereof. The acryloyl and/or methacryloyl compounds of polyoxyalkylenes are obtainable by a process for esterifying or transesterifying acrylic and/or methacrylic acid or acrylic and/or methacrylic esters with a polyoxyalkylene of the general formula (I)

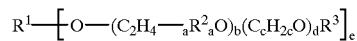

wherein $R^1$, $R^2$, $R^3$ and a–e are as defined in claim 1 and wherein at least one OH group is present per molecule and the sequence of the polyoxyalkylene segments $(C_2H_{4-a}R^2{}_aO)_b$ and $(C_cH_{2c}O)_d$ is arbitrary, in the presence of an enzyme which catalyzes the esterification or transesterification.

12 Claims, No Drawings

PROCESS FOR PREPARING ACRYLIC ESTERS AND/OR METHACRYLIC ESTERS OF POLYOXYALKYLENES AND THE USE THEREOF

FIELD OF THE INVENTION

The present invention relates to a process for preparing acrylic esters and/or methacrylic esters of polyoxyalkylenes in the presence of an enzyme which catalyzes the esterification or transesterification, and to the use thereof.

BACKGROUND OF THE INVENTION

Among raw materials for the preparation of polymer products, the processing of acrylic monomers has undergone rapid development in recent years. Acrylic monomers are used predominantly in the production of fibers, dispersions, raw materials for coatings, raw materials for adhesives, and thermoplastic compositions. In smaller amounts, they serve as starting materials for a variety of chemical syntheses.

In this context, polymers based on acryloyl- and/or methacryloylpolyoxyalkylenes are also of increasing interest. By controlling the variation of the polyoxyalkylene units, it is possible to obtain monomers having a custom-tailored solubility behavior, which can then be reacted alone or in combination with other olefinically unsaturated compounds to form polymers. Compounds of this kind are used, for example, as auxiliaries in the formulation of aqueous inks, as described in DE-A-196 54 752. A further field of use of such compounds is in the dispersion of pigments for preparing water-thinnable coating materials, as is described in EP-A-0 803 556 and JP-A-092 670 34. It is therefore not surprising that acryloyl- and/or methacryloylpolyoxyalkylenes are also obtainable commercially (from Nippon Oil and Fats Co.).

For the purposes of this invention, "acryloyl" or "methacryloyl" means a radical of the general formula:

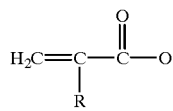

where R is $CH_3$ or H.

Processes for the preparation of acryloyl- and/or methacryloylpolyoxyalkylenes have already been described.

In addition to processes for the esterification and transesterification of acrylates and/or methacrylates, which correspond essentially to literature preparation processes for carboxylic esters, as described, for example, in J. March, Advanced Organic Chemistry, Wiley, 1992, there are also specifically adapted processes which are known in connection with the modification of polyoxyalkylenes.

In this context, it is common to start from hydroxy-functional precursors and to introduce the acryloyl and/or methacryloyl group by esterification or transesterification processes; starting from the corresponding acrylic and/or methacrylic esters or acrylic and/or methacrylic acids. Generally, metal salts or their organic complexes or acids are used in this case. For instance, DE-A-19 535 936 describes the acrylation of polyether polyols with catalysis by p-toluenesulfonic acid and hypophosphorous acid using an azeotrope former and additional free-radical scavengers at temperatures of 80–100° C. This and similar processes are generally carried out at temperatures above 80° C., in particular above 100° C., and require additional stabilization of the reaction mixture by free-radical scavengers (for example methylhydroquinone), in order to reliably suppress unwanted polymerization of the acryloyl and/or methacryloyl compounds at these temperatures.

For many fields of application, the catalyst must subsequently be removed, or at least neutralized, in order to avoid unwanted side reactions. This requires a complex workup procedure, in which metal oxides, metal hydroxides or corresponding salts of the metals and/or of the acids used as catalyst are formed and then, in general, removed by filtration. Such filtrations of acryloyl- and/or methacryloyl-containing reaction mixtures are complex from a technological and industrial safety standpoint and, consequently, are often lengthy.

Because of the high temperature, acryloyl- and/or methacryloyl-functional compounds prepared in this way frequently have an intense coloration (yellow to brownish black). This frequently prohibits the direct use of such acryloyl and/or methacryloyl compounds in applications wherein coloration requirements of the raw materials are stringent (for example, their use as reactive diluents in radiation-curing clearcoats or their use as a raw material for polyacrylates for the cosmetics industry).

In order to avoid some of the disadvantages described above, U.S. Pat. No. 4,528,334 describes a one-pot reaction to carry out the polymerization of acrylic acid in the presence of polyoxyalkylenes; the formation of corresponding polyoxyalkylene-modified polyacrylic acid being achieved at temperatures above 145° C. In the case of this process, the required high temperatures are disadvantageous. Furthermore, the use of other monomers from the important and wide-ranging family of the acrylic and/or methacrylic esters would result in an uncontrollable sequence of transesterification reactions which therefore restrict the process greatly in terms of its variability.

In order to obtain satisfactory yields under mild reaction conditions, it is common to use particularly reactive acrylic and/or methacrylic acid derivatives. Reactions of polyoxyalkylene compounds with acryloyl and/or methacryloyl halides, generally the chlorides, are described, inter alia, in Polym. J., Vol. 17, 827 ff., Polym. Bull., Vol. 15, 425 ff. and Colloid Polym. Sci., Vol. 275, 227–233.

The reaction of acrylic and/or methacrylic anhydrides with polyoxyalkylene compounds is described in Macromolecules, Vol. 30, 6489–6493.

These processes are limited in their spectrum of use as a result of the handleability of the reactive acryloyl and/or methacryloyl halides and acrylic and/or methacrylic anhydrides. Specifically, the requirements with respect to storage conditions; the need to exclude even the slightest trace of moisture; and also the general industrial safety conditions are so high that commercial use of such processes is opposed by an often unjustifiable expense.

R. Tor, Enzyme Micro. Technol., 1990, Vol. 12, April, pp. 299–304, describes the enzymatically catalyzed transesterification of acrylic and methacrylic monomer esters for the preparation of hydroxy- and dihydroxyalkyl acrylates and methacrylates without the formation of di- or triacrylates and -methacrylates. 2-hydroxyethyl, 2-hydroxypropyl and 1,2-dihydroxypropyl esters of acrylic acid and methacrylic acid are investigated in the R. Tor disclosure.

SUMMARY OF THE INVENTION

One object of the present invention is to provide a simplified process for esterifying or transesterifying acrylic and/or methacrylic acid or acrylic and/or methacrylic esters with polyoxyalkylenes, and to provide the reaction products obtainable in this way. Such a preparation process should, in particular, permit a much paler color of the reaction products; should avoid the formation of byproducts (owing to nonselective catalysis); should permit simple removal of the enzyme catalyst from the product; and should avoid unwanted and uncontrolled free-radical polymerizations of the acryloyl and/or methacryloyl compounds. The process should, furthermore, require no complex workup steps whatsoever. Furthermore, the process should not give rise to any of the industrial safety-related disadvantages which occur when highly reactive acrylic and/or methacrylic acid derivatives are used.

The abovementioned object is achieved by acryloyl and/or methacryloyl compounds of polyoxyalkylenes, obtainable by a process for esterifying or transesterifying acrylic and/or methacrylic acid or acrylic and/or methacrylic esters with polyoxyalkylenes of the general formula (I)

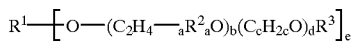

where
R$^1$ is hydrogen, an e-valent, linear or branched, cyclic, unsaturated and/or aromatic hydrocarbon radical, an unsubstituted or substituted aromatic, a carbohydrate or a carbohydrate derivative;
each R$^2$ is the same or different alkyl radicals or alkylene radicals having 1 to 24 carbon atoms or unsubstituted or substituted phenyl radicals having up to 24 carbon atoms;
R$^3$ is a hydrogen radical or a monovalent organic radical;
a is 0 to 3;
b is 0 to 100;
c is 2 to 12;
d is 0 to 100;
e is 1 to 30;
the sum (b+d)=4 to 200; and wherein at least one OH group is present per molecule and the sequence of the polyoxyalkylene segments $(C_2H_{4-a}R^2_aO)_b$ and $(C_cH_{2c}O)_d$ are arbitrary, in the presence of an enzyme which catalyzes the esterification or transesterification reaction.

DETAILED DESCRIPTION OF THE INVENTION

The index "a" in the above formula can adopt different values in one polymer. By this it is intended to express that suitable polyoxyalkylenes may be either, for example, homopolymers of ethylene glycol; copolymers of ethylene glycol and 1,2-propylene glycol; or a multiple copolymer comprising more than two monomers such as ethylene glycol, 1,2-propylene glycol and 1,2-butylene glycol. Independently of this, the index "c" can also adopt different values in one polymer, so that, for example, multiple copolymers may be constructed additionally with 1,4-butylene glycol. The copolymers can be random or blockwise in construction.

The skilled worker is aware that the compounds are in the form of a mixture having a distribution governed essentially by the laws of statistics. The values for the indices b and d therefore represent average values. For the purposes of the present invention, the sum (b+d) is preferably 8 to 120.

Examples of polyoxyalkylenes which can be reacted in accordance with the present invention by enzymatically catalyzed esterification or transesterification with acrylic and/or methacrylic esters or acrylic and/or methacrylic acid are:

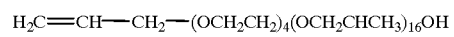
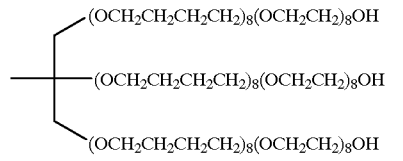
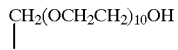
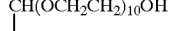
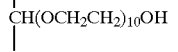
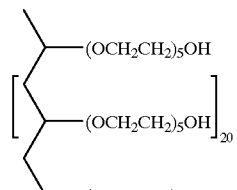
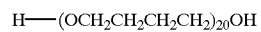
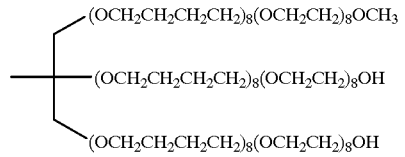
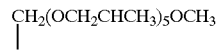
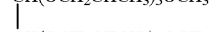

The acryloyl- and/or methacryloylpolyoxyalkylenes according to the present invention are notable because there is at least one acryloyl and/or methacryloyl radical per molecule. It is particularly preferred when from 5 to 100% of the hydroxyl groups have been acrylated and/or methacrylated.

For the purposes of the present invention, the sequence of the constituents of the starting components for preparing the polyoxyalkylenes, as indicated by the indices b and d, is arbitrary and embraces, in particular, not only block copolymers but also random polymer groups and combinations thereof.

A further embodiment of the present invention comprises a process for preparing the abovementioned reaction products.

The inventive process for preparing acryloyl and/or methacryloyl compounds by reacting acrylic and/or methacrylic acid and/or acrylic and/or methacrylic esters with a polyoxyalkylene of the general formula I in the presence of an enzyme which catalyzes the esterification or transesterification is carried out at low temperatures (from 20 to 100° C., preferably from 40 to 70° C.) and under mild conditions. These conditions are advantageous because of the relatively pale color of the product; the avoidance of the formation of byproducts which may otherwise originate, for example, from chemical catalysts; the simple removal of the enzyme catalyst from the product; and the avoidance of unwanted and uncontrolled free-radical polymerization of the acryloyl and/or methacryloyl compounds.

The present invention therefore is directed to the synthesis of acryloyl and/or methacryloyl compounds using enzymes, especially hydrolases, which function as catalysts for esterification and/or transesterification reactions under appropriate conditions, especially lipases, proteases and esterases.

Through the use of enzymes as esterification and/or transesterification catalysts for the preparation of acryloyl- and/or methacryloylpolyoxyalkylenes it is possible to eliminate a large number of the disadvantages of the abovementioned and comparable processes. The synthesis takes place at low temperatures; therefore, the risk of unwanted polymerization of the acryloyl and/or methacryloyl compounds is strongly suppressed. Additionally there is no need to use highly reactive acrylic and/or methacrylic acid derivatives such as halides or anhydrides. Moreover, the enzyme used as the catalyst is easy to separate off.

The acrylation and/or methacrylation proceeds the best, in high yields, with esters of acrylic and/or methacrylic acids as donor molecules, especially methyl, ethyl or butyl acrylate and/or methacrylate.

Enzymes which can be employed, for example, as catalysts in the present invention are hydrolases, especially esterases, lipases and proteases. The enzymes can be employed in pure form or in immobilized form on a support on which they are bound chemically or physically. The amount of the enzyme catalyst, based on the modified polyoxyalkylene employed, is in particular from 0.1 to 20% by weight, preferably from 1 to 10% by weight. The reaction time depends on the amount used and on the activity of the enzyme catalyst, and is, for example, up to 48 hours, preferably up to 24 hours.

In order to arrive rapidly at high degrees of conversion under simple reaction conditions, it is advantageous to use an excess of at least 10% by weight of acrylic acid and/or methacrylic acid and/or their appropriate esters (as donors) in the reaction mixture.

The production system can be characterized either by a stirred tank reactor or by a fixed bed reactor. The stirred tank reactor can be equipped with a means of distillative removal of the alkanol liberated from the acrylic and/or methacrylic acid donor, and/or of the water liberated from the acrylic acid and/or methacrylic acid.

The reaction is carried out until the desired conversion is achieved. A reaction regime with simultaneous distillation is preferred since the removal of the water of reaction and/or alkanol of reaction leads to higher conversions in shorter reaction times, owing to the shifting of the reaction equilibrium.

In order to maximize the degree of conversion, it is necessary to remove the water and/or alkanol of reaction.

After the end of reaction, the enzyme catalyst can be separated off by means of appropriate measures, such as filtration or decantation, and the separated enzyme catalyst may, if desired, be used any number of times.

When a fixed bed reactor is employed, the fixed bed reactor is charged with immobilized enzymes; the reaction mixture being pumped through a column which is packed with catalyst. By using an enzyme immobilized on a support, it is also possible to carry out the reaction in a fluidized bed reactor.

The reaction mixture can be pumped continuously through the column, the residence time and thus the desired conversion being controllable by means of the flow rate. It is also possible to pump the reaction mixture through the column in a circuit, in which case it is also possible to remove the water and/or alkanol of reaction by vacuum distillation at the same time.

Other methods of removing the water and/or alkanol of reaction can also be used, an example being absorption or pervaporation.

A further embodiment of the present invention relates to the use of the acryloyl and/or methacryloyl compounds of the invention as the principal or a secondary constituent for the preparation and/or stabilization of dispersions (solid/liquid and liquid/liquid); as the principal or a secondary constituent in radiation-curing coatings, especially in transparent clearcoats; and as the principal or a secondary constituent for the preparation of polymers by means of free-radical polymerization.

The following example is given to illustrate the present invention and to demonstrate some advantages that can arise from utilizing the same.

EXAMPLE 282 g of a polyoxyalkylene of the general formula $H_2C=CH-CH_2-(OC_2H_4)_{13.5}-OH$ were heated with 226 g of butyl methacrylate and 10 g of Novozym® 435 to 70° C. The butanol liberated was distilled off under vacuum (20–40 mbar). After a reaction time of 16 h, the conversion was 99%. The catalyst was removed was removed by filtration, and excess butyl methacrylate by distillation. The product was pure methacryloylpolyoxyalkylene.

While this invention has been particularly shown and described with respect to preferred embodiments thereof, it will be understood by those skilled in the art that the foregoing and other changes in form and detail may be made without departing from the spirit and scope of the present invention. It is therefore intended that the present invention not be limited to the exact forms described and illustrated, but fall within the scope of the appended claims.

What is claimed is:

1. A process for preparing a modified polyoxyalkylene compound, said process comprising reacting at least one compound selected from the group consisting of acrylic acid, methacrylic acid, acrylic esters and methacrylic esters with a polyoxyalkylene in the presence of an enzyme which catalyzes the reaction, said polyoxyalkylene having the formula I

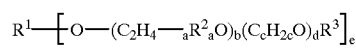

where
R$^1$ is hydrogen, an e-valent, linear or branched, cyclic, unsaturated and/or aromatic hydrocarbon radical, an unsubstituted or substituted aromatic, a carbohydrate or a carbohydrate derivative;
each R$^2$ is the same or different alkyl radicals or alkylene radicals having 1 to 24 carbon atoms or unsubstituted or substituted phenyl radicals having up to 24 carbon atoms;
R$^3$ is a hydrogen radical or a monovalent organic radical,
a is 0 to 3;
b is 0 to 100;
c is 2 to 1.2;
d is 0 to 100;
e is 1 to 30;
the sum (b+d)=4 to 200; and wherein at least one OH group is present per molecule and the sequence of the polyoxyalkylene segments $(C_2H_{4-a}R^2{}_aO)_b$ and $(C_cH_{2c}O)_d$ is random.

2. The process as claimed in claim 1, wherein from 5 to 100% of the hydroxyl groups have been acrylated or methacrylated.

3. The process as claimed in claim 1, wherein the enzyme employed comprises a hydrolase.

4. The process as claimed in claim 3, wherein the hydrolase is selected from the group consisting of a lipase, an esterase and a protease.

5. The process as claimed in claim 1, wherein said enzyme is immobilized on a support.

6. The process as claimed in claim 1, wherein the reaction is carried out at a temperature in the range from 20 to 100° C.

7. The process as claimed in claim 6, wherein the reaction temperature is 40 to 70° C.

8. The process as claimed in claim 1, wherein said compound is at least one of a methyl, ethyl, propyl or butyl ester of methacrylic or acrylic acid.

9. The process as claimed in claim 1, wherein the enzyme is employed in an amount of from 0.1 to 20% by weight, based on the polyoxyalkylene.

10. The process as claimed in claim 9, wherein from 1 to 10% by weight of said enzyme is employed.

11. The process as claimed in claim 1, wherein the enzyme is removed after the reaction.

12. The process as claimed in claim 1, wherein the reaction takes place in a stirred bed reactor or a fixed bed reactor.

* * * * *